United States Patent [19]

Teeple

[11] Patent Number: 4,622,965
[45] Date of Patent: Nov. 18, 1986

[54] ENDOTRACHEAL TUBE

[76] Inventor: Edward Teeple, 641 Ridgefield Ave., Mt. Lebanon, Pa. 15216

[21] Appl. No.: 645,747

[22] Filed: Aug. 30, 1984

[51] Int. Cl.⁴ .......................................... A61M 16/00
[52] U.S. Cl. ........................... 128/207.14; 128/204.25
[58] Field of Search ...................... 128/207.14, 207.15, 128/207.16, 207.17, 750, 752, 760, 768, 772, 303.15, 303.13, 786, 395, 203.27, 657, 658, 204.25; 604/35, 40, 280, 43, 157, 95, 264; 52/195; 222/522-525, 514

[56] References Cited

U.S. PATENT DOCUMENTS 2,091,034  8/1937  Duncan ........................ 128/203.27
3,599,642  8/1971  Tindel ........................... 128/207.14
4,150,676  4/1979  Jackson ............................ 128/657
4,351,328  9/1982  Bodai ............................ 128/207.15

Primary Examiner—Henry J. Recla
Attorney, Agent, or Firm—Reed Smith Shaw & McClay

[57] ABSTRACT

A metal endotracheal tube having a main elongated tubular section and an angularly offset anterior portion. A second tubular member is telescopically positioned over the anterior portion with a biasing spring interpositioned to normally maintain the second member spaced apart from the anterior portion. A control mechanism is mounted alongside of the tube to control the biased movement of the second member.

5 Claims, 4 Drawing Figures

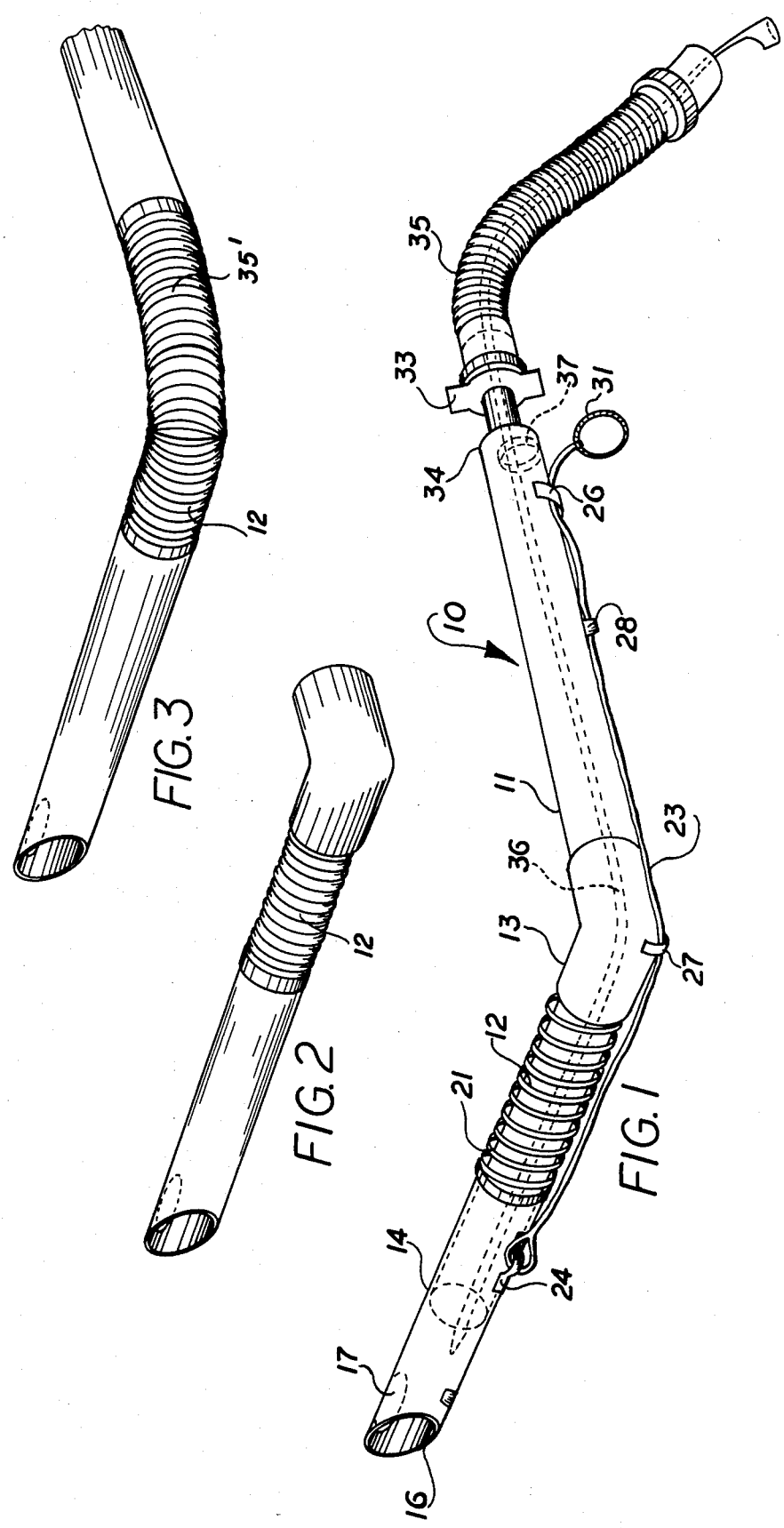

ENDOTRACHEAL TUBE

FIELD OF THE INVENTION

The present invention relates to an endotracheal tube, and, in particular, a metal endotracheal tube having a telescoping distal end member.

BACKGROUND OF THE INVENTION

Various forms and types of endotracheal tubes are known within the art. Many improvements have been made to such tubes which are the subject of numerous patents.

Endotracheal tubes are tubes which are inserted into the trachea which connects the larynx and the bronchi in the human body. Typically, these tubes are used by anesthesiologists in the application of an inhalation anesthetic. Endotracheal tubes are also used in facilitating the breathing of a patient while the patient is under anesthesia by keeping the airway open.

Prior art endotracheal tubes were originally constructed from rubber body portions having metal fittings such as adapters and connectors. More recently, however, such tubes have been constructed out of synthetic resinous materials such as polyethylene or polypropylene. These materials have the advantage that they are easily sterilizable by ethylene oxide, inexpensive and disposal after use. However, prior art endotracheal tubes made from rubber or synthetic resinous compounds are flammable and can catch fire during procedures in which medical laser beams are utilized in the vicinity of the distal end of the tube.

Accordingly, it is an object of the present invention to provide an endotracheal tube made of metal which will eliminate the possibility of fire during procedures utilizing a laser beam. It is a further object of the present invention to provide a metal endotracheal tube having a spring biased distal end to facilitate positioning of the tube through the larynx into the trachea.

SUMMARY OF THE INVENTION

The present invention overcomes many of the disadvantages inherent in prior art endotracheal tubes, in particular, prior art tubes made from synthetic resinous materials. In general, the present invention comprises an endotracheal tube made of metal, such as copper or stainless steel, having a telescoping distal anterior end portion. The endotracheal tube of the present invention includes a main elongated tubular section and an angularly offset portion adjacent the anterior portion of the tube. The offset is provided either by a fixed or hinged joint or a flexible coupling positioned within the tube. A second tubular member having an inner diameter slightly larger than the outer diameter of elongated main section which is adapted to concentrically fit over the anterior end of the main section and define the distal end of the endotracheal tube. The second member includes a flanged and bevelled tip at its end.

A stop means is positioned adjacent the joint on the main section of the tube for restraining a biasing means. A biasing means, preferably a coil spring, is concentrically positioned over the anterior portion of the main tubular section between said stop and the end of the second tubular member. A coil spring is adapted to bias the second tubular member away from the joint or stop means of the main tubular section. A control means, preferably a wire, is securely attached to the second tubular section and routed to the opposite end of the main tubular section for controlling the travel of said secondary member.

In general, the endotracheal tube of the present invention is connected to a source of anesthesic gases by means of a connector at one end of the main tubular section. The anesthesiologist retracts the second tubular member by pulling the control wire and compressing the biasing means. The distal portion of the tube is inserted through a patient's mouth until it reaches the larynx. At that point, the anesthesiologist permits the biasing means to decompress and slowly extending the distal end of second tubular member through the vocal cords into the trachea by slow release of the control means. By permitting the biasing means to slowly decompress and extend the distal end of the second tubular member through the vocal cords, the damage associated with the insertion of endotracheal tubes of the prior art can be greatly reduced. Other advantages of the present invention become apparent from a perusal of the following description of a presently preferred embodiment taken in connection with the accompanying drawings.

BRIEF DESCRIPTION OF THE DRAWINGS

FIG. 1 is a perspective view of the endotracheal tube where the distal end of the second tubular section is fully extended;

FIG. 2 is a partial view in the perspective showing the distal end fully retracted;

FIG. 3 is a partial view of the endotracheal tube in an alternative embodiment a flexible elbow to permit variance angles.

PRESENTLY PREFERRED EMBODIMENT

Figure 4:
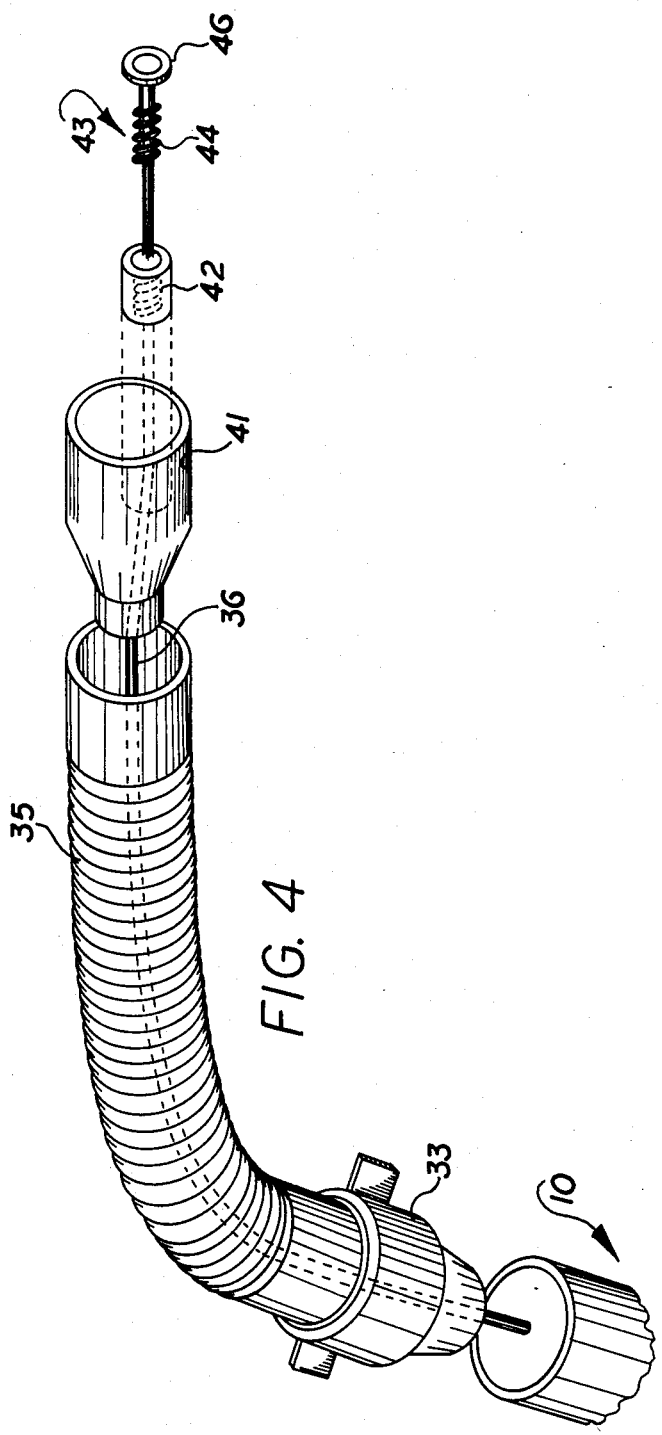
FIG. 4 is an exploded view of a preferred embodiment of a CVP catheter holder for use with endotracheal tubes.

Referring to FIG. 1, endotracheal tube 10 of the present invention comprises a main elongated section 11 and an offset anterior portion 12. Anterior portion 12 is formed from section 11 by the inclusion of a fixed or hinged joint 13 or by incorporation therein of the flexible joint made of stainless steel or the like. If joint 13 is fixed, it is preferably fixed at a complementary 135° angle. Main section 11 is made from metal cylindrical tubing, preferably copper or stainless steel, having an inner diameter of approximately 6.1 mm and an outer diameter of approximately 6.5 mm. The overall length of main member 11 is approximately 29 mm. Anterior portion 12 of the main tubular member is approximately 7 cm in length and has a total outer diameter of approximately 5.9 to 6.0 mm. A second tubular member 14 is adapted to fit over anterior portion 12 of tube 10. Second tubular member 14 is approximately 5 cm in length and has an inner diameter of only slightly greater than the outer diameter of anterior portion 12, i.e., approximately 6.1 mm. It is preferably, but not necessary, that a partial seal be effected during the telescoping of the two members. The outer diameter of second tubular member 14 is approximately 6.5 mm and includes bevelled tip 16. Opening 17 is provided adjacent bevelled end 16 to prevent wall occlusions.

Positioned concentrically over anterior portion 12 and between joint 13 and second tubular member 14 is spring 21. Preferably, spring 21 has an outer diameter equal to or slightly less than the outer diameter of second tubular member 14 and joint 13. Preferably, compression spring 21 is approximately 3.75 cm in length and has sufficient spring force to urge second tubular member 14 away from joint 13 when the spring is fully compressed as shown in FIG. 2.

A control wire 23 is attached between second member 14 and main member 11 by retaining means 24 and 26, respectively. Additionally, guides 27 and 28 may be used to maintain control wire 23 in juxtapose position to the endotracheal tube 10. Preferably, control wire 23 includes loop 31 adapted to fix around an attending physician's finger. Retainer 26 is positioned relative to loop 31 to prevent second tubular member 14 from moving beyond the anterior section 12.

In the embodiment where joint 13 is flexible, as shown in FIG. 3, a connector 35' similar to that used as flexible connector 35 is suitable. It is also clear that either or both spring 21 and control wire 23 could be positioned within tube 10.

As shown in FIG. 1, a connector piece 33 is fixed within end 34 of main tubular member 11. Connector piece 33 is well known and available to the art for connecting prior art endotracheal tubes to flexible connector 35 for subsequent connection to a source of anesthetic. Also shown connected within endotracheal tube 10 ventilator catheter 36. Catheter 36 is restrained within the tube 10 by means of interior loops 37.

However, a preferred catheter holding means is shown in FIG. 4. In this embodiment, end piece 41 fits into flexible connector 35. In the preferred embodiment, end piece 41 is of metal and partially funnel-shaped so as funnel the catheter 36 into connector 35. Cylindrical holder 42 is secured within end piece 41 by welding, or the like, and is of an inner diameter to permit catheter head 43 to connect to catheter body 36. Threaded portion 44 preferably screws into internal threads tapped within holder 42. Lip 46 allows the connection of the catheter head 43 to a jet ventilator (not seen).

By means of this holder, the catheter can be readily changed with each use or if it catches fire during a procedure it can be quickly removed without the necessity of withdrawing the endotracheal tube.

While a presently preferred embodiment of the invention has been shown and described in particularity, the invention may be otherwise embodied within the scope of the appended claims.

What is claimed is:

1. A metal endotracheal tube adapted for use in laser beam surgery comprising:
   a. a main elongated tubular member having an anterior portion angularly offset therefrom and terminating in an open end;
   b. a second metallic tubular member having one end portion positioned over the anterior portion of said main tubular member;
   c. stop means positioned on the anterior portion adjacent said angular offset;
   d. biasing means positioned between said stop means and the telescopic end of said second tubular member for biasing said second member away from said main member; and
   e. control means operably connected to said second tubular member from moving said member with respect to said biasing means.

2. A metallic endotracheal tube as claimed in claim 1, wherein said anterior portion includes a tubular member having an outer diameter slightly less than the outer diameter of said main member and said stop means comprises an angular joint formed by said anterior portion and said main member.

3. A metal endotracheal tube as claimed in claim 2, wherein said joint comprises one of a rigid of flexible hinge.

4. A metal endotracheal tube as claimed in claim 1, wherein said control means comprises a wire slidably secured along said main tubular member and having one end secured to said second tubular member and an opposite end terminating in a finger loop.

5. A metal endotracheal tube as claimed in claim 1 including a funnel shaped end piece positioned within the end of the main tubular member opposite said open end, a cylindrical holder secured within the end piece and a catheter means having one end of extending through said funnel shaped end piece and into said main tubular member and an opposite end securely positioned within said cylindrical holder, said second and also including means adapted to be connected to a ventilator means.

* * * * *

UNITED STATES PATENT AND TRADEMARK OFFICE
CERTIFICATE OF CORRECTION

PATENT NO. : 4,622,965

DATED : November 18, 1986

INVENTOR(S) : Edward Teeple

It is certified that error appears in the above-identified patent and that said Letters Patent is hereby corrected as shown below:

Column 4, line 10, after "portion" insert -- telescopically --.

Column 4, line 28, after "rigid" delete "of" and substitute therefor -- or --.

Signed and Sealed this

Third Day of March, 1987

*Attest:*

DONALD J. QUIGG

*Attesting Officer*  *Commissioner of Patents and Trademarks*